US00PP13218P2

(12) United States Plant Patent
Hammond

(10) Patent No.: US PP13,218 P2
(45) Date of Patent: Nov. 12, 2002

(54) ARGYRANTHEMUM PLANT NAMED 'M8/20'

(76) Inventor: Francis William Hammond, 100 Boundary Road, Narre Warren East, 3804, Victoria (AU)

( * ) Notice: Subject to any disclaimer, the term of this patent is extended or adjusted under 35 U.S.C. 154(b) by 4 days.

(21) Appl. No.: 09/873,044

(22) Filed: Jun. 4, 2001

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Argyranthemum plant named 'M8/20', characterized by its compact and mounded plant habit; freely branching habit, dense and bushy plants; very freely flowering with numerous inflorescences per plant; purple red-colored ray florets that fade to pale pink with age; and unique semi-double inflorescence form.

1 Drawing Sheet

BACKGROUND OF THE INVENTION

The present invention relates to a new and distinct cultivar of Argyranthemum plant, botanically known as *Argyranthemum frutescens* and hereinafter referred to by the name 'M8/20'.

The new Bracteantha is a product of a planned breeding program conducted by the Inventor in Narre Warren East, Victoria, Australia. The objective of the program is to creat and develop new compact Argyranthemum cultivars with numerous inflorescences with attractive ray floret coloration.

The new Argyranthemum originated from a cross by the Inventor of the *Argyranthemum frutescens* cultivar M5/18, not patented, as the female, or seed, parent with an unidentified proprietary selection of *Argyranthemum frutescens*, not patented, as the male, or pollen, parent. The new Argyranthemum was discovered and selected by the Inventor as a plant within the progeny of the stated cross in a controlled environment in Narre Warren East, Victoria, Australia on Mar. 1, 1999. The selection of the new Argyranthemum was based on its compact mounded plant habit, purple red-colored ray florets and unique inflorescence form.

Asexual reproduction of the new Argyranthemum by terminal cuttings taken in a controlled environment in Narre Warren East, Victoria, Australia, since Mar. 1, 1999, has shown that the unique features of this new Argyranthemum are stable and reproduced true to type in successive generations.

The new Argyranthemum has not been observed under all possible environmental conditions. The phenotype may vary somewhat with variations in environment such as temperature, daylength, light intensity, photoperiod, and water and nutritional status without, however, any variance in genotype.

The following characteristics have been repeatedly observed and are determined to be basic characteristics of 'M8/20' and distinguish the new Argyranthemum as a new and distinct cultivar:

1. Compact and mounded plant habit.
2. Freely branching habit, dense and bushy plants.
3. Very freely flowering with numerous inflorescences per plant.

4. Purple red-colored ray florets that fade to pale pink with age.
5. Unique semi-double inflorescence form.

Plants of the new Argyranthemum differ from plants of the parent cultivar M5/18 primarily in inflorescence form and ray floret color as plants of the cultivar M5/18 have single inflorescence form and pink-colored ray florets. In addition, plants of the new Argyranthemum have a dense, compact and mounded in plant habit whereas plants of the cultivar M5/18 have an open and loose plant habit. Plants of the male parent, the unidentified selection of Argyranthemum, differ primarily from plants of the new Argyranthemum in ray floret color and inflorescence form.

Plants of the new Argyranthemum are comparable to plants of the cultivar Summer Melody, disclosed in U.S. Plant Pat. No. 11,763. In side-by-side comparisons conducted by the Inventor in Narre Warren East, Victoria, Australia, plants of the new Argyranthemum differ from plants of the cultivar Summer Melody in the following characteristics:

1. Plants of the new Argyranthemum are more compact and shorter than plants of the cultivar Summer Melody.
2. Plants of the new Argyranthemum have smaller leaves than plants of the cultivar Summer Melody.
3. Inflorescences of plants of the new Argyranthemum are semi-double in form whereas inflorescences of plants of the cultivar Summer Melody are double in form.
4. Plants of the new Argyranthemum have narrower peduncles than plants of the cultivar Summer Melody.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Argyranthemum.

The photograph at the top of the sheet comprises a side perspective view of a typical plant of 'M8/20'.

The photograph at the bottom of the sheet comprises a close-up view of typical inflorescences of 'M8/20'. Plants used in the photographs were about 12 weeks from planting rooted cuttings.

DETAILED BOTANICAL DESCRIPTION

The following observations, measurements and values describe plants grown in Narre Warren East, Victoria, Australia, under outdoor conditions with day temperatures ranging from 18 to 32° C., night temperatures ranging from 6 to 25° C., and full sunlight. Rooted liners of the new Argyranthemum were planted in 20-cm containers and grown for about 12 weeks. Color references are made to The Royal Horticultural Society Colour Chart except where general terms of ordinary dictionary significance are used.

Botanical classification: *Argyranthemum frutescens* cultivar M8/20.

Parentage:

*Female or seed parent.*—*Argyranthemum frutescens* cultivar M5/18, not patented.

*Male or pollen parent.*—Unidentified proprietary selection of *Argyranthemum frutescens*, not patented.

Propagation:

*Type.*—Terminal tip cuttings.

*Time to initiate roots.*—About 7 to 14 days at 22° C.

*Time to produce a rooted cutting.*—About 30 days at 20 to 28° C.

*Root description.*—Fine, fibrous.

Plant description:

*General appearance.*—Compact and bushy growth habit; mounded plant form with dense foliage and inflorescences held above the foliage on long peduncles. Freely branching, about 24 lateral branches per plant. Appropriate for 15 to 20-cm containers.

*Crop time.*—Rapid growth rate; to produce a finished 20-cm containerized plant from rooted cuttings, about 12 weeks are required.

*Plant height.*—About 22 cm.

*Plant width.*—About 36 cm.

*Lateral branch description.*—Quantity per plant: About 30 to 35. Length: About 14 cm. Width: About 4 mm. Aspect: Mostly upright. Cross-section: Hexagonal. Texture: Smooth, glabrous. Color: 146C.

*Foliage description.*—Arrangement: Single, mostly opposite; clasping, sessile. Length: About 5 cm. Width: About 2 cm. Shape: Bipinnatisect. Apex: Acute. Base: Acuminate. Margin: Serrate. Texture, both surfaces: Smooth, glabrous. Venation pattern: Parallel. Color: Young foliage, upper surface: 143A. Young foliage, lower surface: 143C. Mature foliage, upper surface: 189A. Mature foliage, lower surface: 147B. Venation, upper surface: 147C. Venation, lower surface: 146C.

Inflorescence description:

*Appearance.*—Flat semi-double composite inflorescence form with elliptic-shaped ray florets. Inflorescences held upright on axillary peduncles. Disc and ray florets arranged acropetally on a capitulum. Inflorescences persistent. Inflorescences not fragrant. Inflorescences last about one week on the plant.

*Flowering response.*—Under natural conditions, plant flower from spring to early fall; plants flower continuous during this period.

*Quantity of inflorescences.*—Very freely flowering with about 130 to 150 flower buds and inflorescences per plant.

*Inflorescence size.*—Diameter: About 5 cm. Depth (height): About 1.5 cm. Diameter of disc: About 1 cm. Receptacle diameter: About 1.45 cm. Receptacle height: About 7.5 mm.

*Flower buds.*—Height: About 8 mm. Diameter: About 8 mm. Shape: Roughly spherical. Color: 146B.

*Ray florets.*—Quantity per inflorescence: About 60 to 70 arranged in 4 or 5 whorls. Shape: Elliptic. Length: About 2 cm. Width: About 5 mm. Apex: Emarginate. Base: Acute. Margin: Entire. Texture, both surfaces: Smooth, satiny, glabrous. Aspect: Initially upright; when mature, about 90° from vertical, perpendicular to peduncle. Color: When opening, upper surface: 63A. When opening, lower surface: 70C. Fully opened, upper surface: 63B. Fully opened, lower surface: 65A; fading to 69A with age.

*Disc florets.*—Arrangement: Massed at the center of the inflorescence. Shape: Tubular, flared at apex. Color: Immature: 2C. Mature: 3A.

*Peduncle.*—Strength: Moderately strong to strong. Aspect: Upright. Length: About 8 to 11 cm. Diameter: About 1.5 mm. Texture: Smooth, glabrous. Color: 144A.

*Involucral bracts.*—Quantity: About 17 to 20. Length: About 5 mm. Width: About 2.25 mm. Shape: Ovate. Apex: Acute. Base: Cuneate. Margin: Entire. Texture, both surfaces: Smooth, glabrous. Color, both surfaces: Yellowish green.

*Reproductive organs.*—Androecium: Present on disc florets only. Amount of pollen: Moderate. Color: Yellowish. Gynoecium: Present on both ray and disc florets.

*Seed.*—Seed production has not been observed.

Disease resistance: Resistance to pathogens common to Argyranthemum has not been observed on plants grown under commercial conditions.

Temperature/weather tolerance: Plants of the new Argyranthemum have been observed to be tolerant to temperatures as low as −2° C. and temperatures as high as 40° C. Plants of the new Argyranthemum have been observed to be tolerant to rain and wind.

It is claimed:

1. A new and distinct cultivar of Argyranthemum plant named 'M8/20', as illustrated and described.

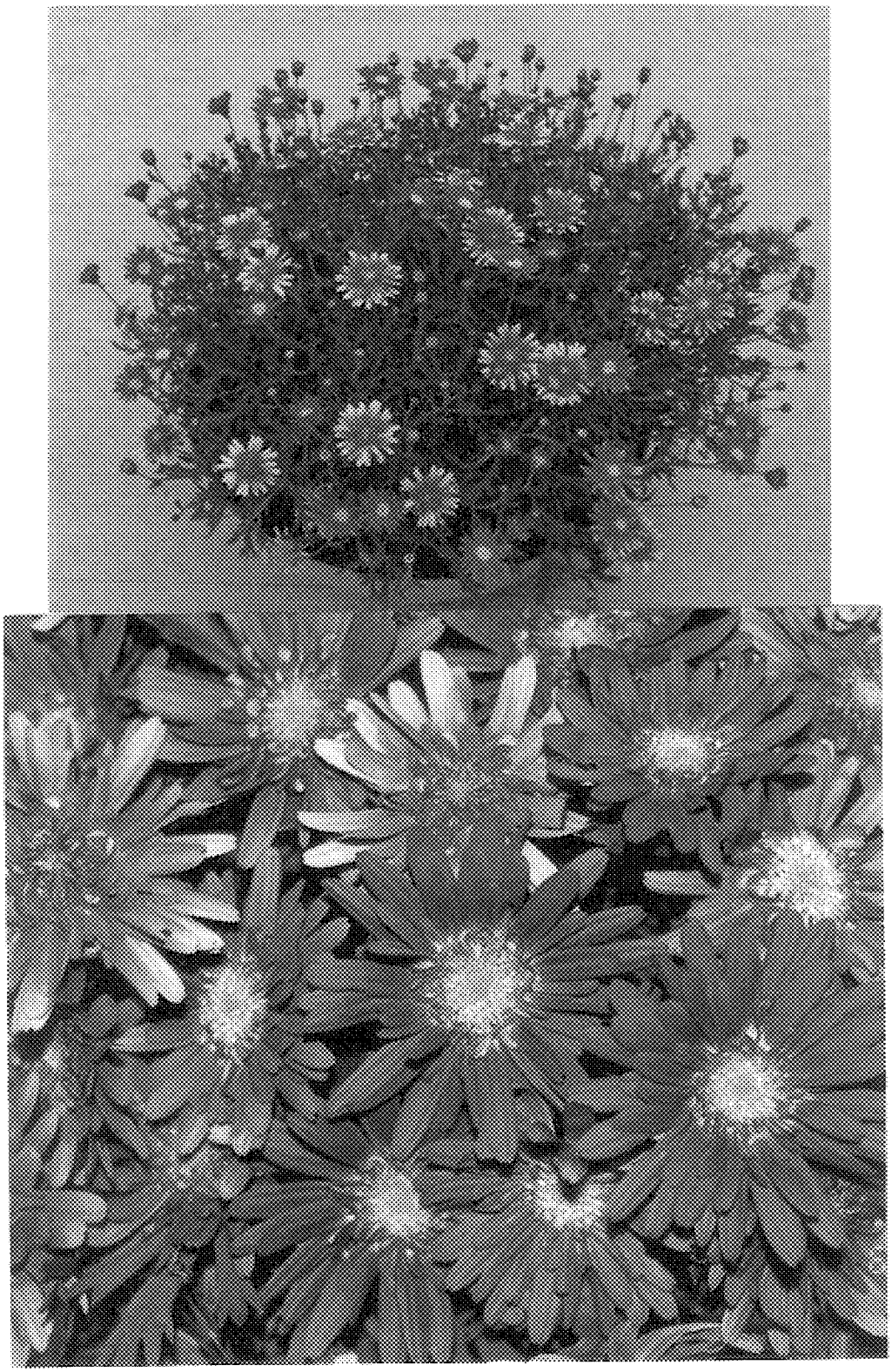

* * * * *